United States Patent
Mizuta et al.

(10) Patent No.: US 9,134,441 B2
(45) Date of Patent: Sep. 15, 2015

(54) TOMOGRAPHIC EQUIPMENT, IMAGING SYSTEM PROVIDED THEREWITH, AND IMAGING DATA ACQUISITION METHOD

(75) Inventors: Tetsuro Mizuta, Kyoto (JP); Keishi Kitamura, Kyoto (JP); Yuichi Inaoka, Kyoto (JP); Munehiro Takahashi, Kyoto (JP); Michio Senda, Kobe (JP); Keiichi Matsumoto, Kobe (JP); Keiji Shimizu, Kobe (JP)

(73) Assignees: SHIMADZU CORPORATION, Kyoto (JP); FOUNDATION FOR BIOMEDICAL RESEARCH AND INNOVATION, Hyogo (JP)

( * ) Notice: Subject to any disclaimer, the term of this patent is extended or adjusted under 35 U.S.C. 154(b) by 1158 days.

(21) Appl. No.: 12/933,820

(22) PCT Filed: Mar. 26, 2008

(86) PCT No.: PCT/JP2008/055736
§ 371 (c)(1),
(2), (4) Date: Sep. 21, 2010

(87) PCT Pub. No.: WO2009/118843
PCT Pub. Date: Oct. 1, 2009

(65) Prior Publication Data
US 2011/0019895 A1 Jan. 27, 2011

(51) Int. Cl.
*G06K 9/00* (2006.01)
*G01T 1/29* (2006.01)
*G01T 1/16* (2006.01)
(Continued)

(52) U.S. Cl.
CPC ............... *G01T 1/2985* (2013.01); *A61B 6/037* (2013.01); *G01T 1/1603* (2013.01); *G01T 1/1611* (2013.01)

(58) Field of Classification Search
None
See application file for complete search history.

(56) References Cited

U.S. PATENT DOCUMENTS 7,113,873 B2 * 9/2006 Hoyte et al. ............... 702/50
7,709,801 B2 * 5/2010 Ooi ............................ 250/367
(Continued)

FOREIGN PATENT DOCUMENTS

JP 7-113873 A 5/1995
JP 2000-28727 A 1/2000
(Continued)

OTHER PUBLICATIONS

Matsumoto et al ( comparision of noise equivalent count rate and image quality for 2D and 3D PET scans)Aug. 2006.*
(Continued)

*Primary Examiner* — Nancy Bitar
(74) *Attorney, Agent, or Firm* — Cheng Law Group, PLLC

(57) ABSTRACT

A cross-sectional area calculation section calculates a cross-sectional area of a subject as physical quantity with respect to a size of the subject, and an NEC calculation section calculates a noise equivalent count NEC as physical quantity for evaluating an image. The C-NEC calculation section calculates a noise equivalent count per unit area C-NEC as physical quantity for evaluating an image as per size of the subject in accordance with the cross-sectional area of the subject calculated in the cross-sectional area calculation section and the noise equivalent count NEC calculated in the NEC calculation section. Accordingly, the noise equivalent count per unit area C-NEC is calculated as noted above, whereby an index may be determined that is independent of the cross-sectional area of the subject in evaluating the image.

17 Claims, 7 Drawing Sheets

(51) Int. Cl.
*G01T 1/161* (2006.01)
*A61B 6/03* (2006.01)

(56) References Cited

U.S. PATENT DOCUMENTS

| | | | |
|---|---|---|---|
| 8,059,880 B2* | 11/2011 | Mizuta et al. | 382/131 |
| 2006/0067578 A1* | 3/2006 | Fuse | 382/190 |
| 2009/0169082 A1* | 7/2009 | Mizuta et al. | 382/131 |
| 2009/0179154 A1* | 7/2009 | Ooi | 250/369 |

FOREIGN PATENT DOCUMENTS

| | | |
|---|---|---|
| JP | 2006-184152 A | 7/2006 |
| JP | 2006-262963 A | 10/2006 |

OTHER PUBLICATIONS

Matsumoto, Keiichi et al., "Comparison of Noise Equivalent Count Rate and Image Quaity for Two-dimensional and Three-dimensional PET Scans", Japanese Journal of Radiology Technology, vol. 62, No. 8, pp. 1111-1118, Apr. 12, 2006.

International Search Report for the Application No. PCT/JP2008/055736 mailed May 1, 2008.

Matsumoto, Keiichi et al., "Comparison of Noise Equivalent Count Rate and Image Quality for Two-dimensional and Three-dimensional PET Scans", Japanese Journal of Radiological Technology, vol. 62, No. 8, pp. 1111-1118, Apr. 12, 2006.

* cited by examiner

TOMOGRAPHIC EQUIPMENT, IMAGING SYSTEM PROVIDED THEREWITH, AND IMAGING DATA ACQUISITION METHOD

TECHNICAL FIELD

This invention relates to tomographic equipment, an imaging system provided therewith, and a method of acquiring imaging data for performing coincidence of radiation generated from a subject with radiopharmaceutical administered thereto to obtain a sectional image.

BACKGROUND ART

PET (Positron Emission Tomography) equipment reconstructs sectional images of a subject only upon detection of positron, i.e., two or more gamma rays generated in annihilation of the positron and, detection of the gamma rays simultaneously with two or more detectors.

The PET equipment of this type doses a subject with a radioactive drug, and thereafter determines accumulation of the drug in a target tissue temporally. As a result, various body functions may be determined quantitatively. Consequently, an image that the PET equipment obtains has functional information.

Here, in techniques to simultaneously detect gamma rays, i.e. to perform coincidence of gamma rays, a 3D-PET that detects gamma rays three-dimensionally has been recently used besides a 2D-PET that detects gamma rays two-dimensionally. In such 3D-PET, each of the detectors is arranged close to the subject at a large solid angle, which results in enhanced detection efficiency of gamma rays and significantly improved system sensitivity.

For performing coincidence of gamma rays, each of gamma rays is inputted into a coincidence circuit to determine on whether or not a time lag of the inputted gamma rays is kept within a given time window. In an actual coincidence circuit, gamma rays are typically considered "coincident" that are detected in an extremely short time window of around 4 ns to 20 ns (ns=$10^{-9}$ s). Consequently, there arises a possibility of performing coincidence of each one of gamma rays generated at two different points. This is called "random, coincidence count." FIG. 12($a$) is a schematic view exemplarily showing a state of the random coincidence. On the other hand, where coincidence is performed after one or both of a pair of gamma rays causes Compton scattering within the subject, the coincidence is called "scatter coincidence count." FIG. 12($b$) is a schematic view exemplarily showing a state of the scatter coincidence. A portion shown in the detector in FIG. 12 by hatching illustrates a detector that performed coincidence. Where coincidence of both a pair of gamma rays is normally performed, the coincidence is called "true coincidence count" (see, for example, Patent Literatures 1, 2).

In order to enhance image quality of the PET, it needs to increase the number of true coincidence counts (T) to enhance statistical accuracy, and also to suppress noise amplification in various corrections. As for an approach to enhance statistical accuracy, a dosage of radiopharmaceutical may be increased or a data acquisition time to perform coincidence for data acquisition may be extended. However, even if the true coincidence count (T) doubles by increasing dosage by twice, the random coincidence count (R) will increase by 4 times, which results in increased noise amplification in correction of the random coincidence count. In addition, scattered coincidence count (S) is to be included that varies depending on a size of the subject and distribution of radioactivity. Here, noise equivalent count (NEC: Noise Equivalent Count) is used as an index of simple evaluation of the PET image quality from the counts T, S, and R (see, for example, Non-Patent Literature 1.)

Where the random coincidence count is measured and corrected, the noise equivalent count NEC is given by the following equation (1) using a circuit that is a combination of the coincidence circuit with a delay circuit (delayed coincidence circuit). Moreover, where the random coincidence count is estimated and corrected from a single counting rate, the noise equivalent count NEC is given by the following equation (2).

$$NEC=T^2/(T+S+2\times f\times R) \quad (1)$$

$$NEC=T^2/(T+S+f\times R) \quad (2)$$

Where, f in the foregoing equations (1) and (2) is a ratio of the subject to a gantry with a gamma-ray detector being embedded therein. Specifically, the rate is a rate of the subject to an aperture diameter of the gantry (i.e., an aperture diameter of the gamma-ray detector.)

[Patent Literature 1]
Japanese Patent Publication No. 2000-28727 (page 3, FIG. 5)
[Patent Literature 2]
Japanese Patent Publication No. H07-113873 (page 1-7 and 9-11, FIGS. 2, 5, 7, 8 and 13)
[Non-Patent Literature 3]
Keiichi Matsumoto and other 5 persons: "Comparison of Noise Equivalent Count Rate and Image Quality of Two-dimensional and Three-dimensional PET Scans", Japanese Journal of Radiological Technology, Vol. 62, No. 8, P1111-1118 (2006.8)

DISCLOSURE OF THE INVENTION

Problem to be Solved by the Invention

However, the noise equivalent count NEC has a problem that a size of the subject fails to be under consideration. For instance, in comparison of the PET images of the subjects in large and small sizes having an equal noise equivalent count, a condition arises that higher image quality may be obtained for the subject in small size (for example, a standard deviation in a uniform region is small.) That is because the noise equivalent count NEC is distributed in a reconstruction area, and thus a larger reconstruction area (i.e., the subject in larger size) has a smaller noise equivalent count per unit area, and a smaller reconstruction area (i.e., the subject in small size) has a larger noise equivalent count per unit area. In other words, there is a problem that an approach in conventional techniques as Non-Patent Literature 1 that estimates image quality from the noise equivalent count is not established to subjects having different sizes. Consequently, physical quantity represented by the noise equivalent count that evaluates an image does not act as an index of image quality evaluation when the physical quantity with respect to a size of the subject represented by an area differs to each other.

In addition, the noise equivalent count is subsequently calculated from information on total numbers after imaging, and thus is merely an index for examining a subsequent imaging condition based on the calculated noise equivalent count. Accordingly, it is necessary to determine an extent of image quality to be secured during imaging.

This invention has been made regarding the state of the art noted above, and its object is to provide tomographic equipment that allows determination of an index independent of physical quantity with respect to a size of a subject, an imaging system provided therewith, and a method of acquiring imaging data.

Means for Solving the Problem

This invention is constituted as stated below to achieve the above object. Tomographic equipment of this invention is tomographic equipment that performs coincidence of radiation generated from a subject with radiopharmaceutical administered thereto to obtain a sectional image. The tomographic equipment includes a first physical quantity calculation device that calculates physical quantity with respect to a size of the subject, a second physical quantity calculation device that calculates physical quantity for evaluating an image, and a third physical quantity calculation device that calculates physical quantity for evaluating an image per size of the subject in accordance with the physical quantity calculated by the first physical quantity calculation device and the physical quantity calculated by the second physical quantity calculation device.

The tomographic equipment according to this invention includes the first physical quantity calculation device, the second physical quantity calculation device, and the third physical quantity calculation device. The first physical quantity calculation device calculates physical quantity with respect to a size of the subject, and the second physical quantity calculation device calculates physical quantity for evaluating an image. The third physical quantity calculation device calculates physical quantity for evaluating an image per size of the subject in accordance with the physical quantity calculated by the first physical quantity calculation device and the physical quantity calculated by the second physical quantity calculation device. The physical quantity with respect to the size of the subject is calculated as noted above, whereby an index may be determined that is independent of the physical quantity with respect to the size of the subject.

The imaging system of this invention includes tomographic equipment that performs coincidence of radiation generated from a subject with radiopharmaceutical administered thereto to obtain a sectional image, and imaging equipment that conducts predetermined imaging to the subject for obtaining a given image. The imaging system includes a first physical quantity calculation device that calculates physical quantity with respect to a size of the subject, a second physical quantity calculation device that calculates physical quantity for evaluating an image, and a third physical quantity calculation device that calculates physical quantity for evaluating an image per size of the subject in accordance with the physical quantity calculated by the first physical quantity calculation device and the physical quantity calculated by the second physical quantity calculation device.

The imaging system according to this invention includes the tomographic equipment and the imaging equipment. Here, the tomographic equipment includes the first physical quantity calculation device, the second physical quantity calculation device, and the third physical quantity calculation device, which is similar to the invention concerning the tomographic equipment. The first physical quantity calculation device calculates physical quantity with respect to a size of the subject, and the second physical quantity calculation device calculates physical quantity for evaluating an image. The third physical quantity calculation device calculates physical quantity for evaluating an image per size of the subject in accordance with the physical quantity calculated by the first physical quantity calculation device and the physical quantity calculated by the second physical quantity calculation device. Accordingly, the physical quantity with respect to the size of the subject is calculated as noted above, whereby an index may be determined that is independent of the physical quantity with respect to the size of the subject.

As one embodiment of the foregoing tomographic equipment and the imaging equipment provided therewith, the tomographic equipment includes an external radiation source that externally irradiates a subject with radiation of a same form as radiopharmaceutical, and a first physical quantity calculation device calculates physical quantity with respect to a size of the subject in accordance with radiation that is applied by the external radiation source and transmitted through the subject. Data acquired based on radiation that is applied from the external radiation source and transmitted through the subject (for instance, transmission data) has form information on the subject. Consequently, the first physical quantity calculation device may simply calculate the physical quantity with respect to the size of the subject in accordance with the radiation.

As another embodiment of the foregoing tomographic equipment and the imaging equipment provided therewith, the first physical quantity calculation device calculates physical quantity with respect to the size of the subject in accordance with form information on the subject that is obtained from external equipment seen from the tomographic equipment (corresponding to the external equipment in the invention concerning the tomographic equipment, the imaging equipment in the invention concerning the imaging system.) Since data obtained from the external equipment is form information on the subject, the first physical quantity calculation device may simply calculate the physical quantity with respect to the size of the subject in accordance with the form information.

Here, data as a basis for calculating the physical quantity with respect to the size of the subject by the first, physical quantity calculation device is not limited to the form information of the subject. Even when data is functional information on the subject (for instance, emission data), it is possible to calculate the physical quantity with respect to the size of the subject since a distribution of radioactivity in the subject that spreads with the radiopharmaceutical may show a contour of the subject.

Moreover, the foregoing external equipment seen from the tomographic equipment (corresponding to the external equipment in the invention concerning the tomographic equipment, the imaging equipment in the invention concerning the imaging system) is X-ray CT equipment. Calculation is to be performed as follows in accordance with form information on the subject when the first physical quantity calculation device calculates the physical quantity with respect to the size of the subject. Specifically, the X-ray CT equipment obtains a CT image, and thus the CT image has form information. The first physical quantity calculation device calculates the physical quantity with respect to the size of the subject in accordance with the CT image.

The external equipment seen from the tomographic equipment (corresponding to the external equipment in the invention concerning the tomographic equipment, the imaging equipment in the invention concerning the imaging system) is not limited to an X-ray CT apparatus. Moreover, form information is not limited to a CT image. Equipment is applicable that obtains a given image by conducting predetermined imaging to the subject and data having form information. For instance, an image obtained by nuclear magnetic resonance imaging (MRI: Magnetic Resonance Imaging) equipment has form information. Consequently, the first physical quantity calculation device may calculate the physical quantity with respect to the size of the subject in accordance with the form information obtained from the MRI equipment.

In the foregoing tomographic equipment and the imaging system provided therewith, an example of the physical quantity with respect to the size of the subject calculated by the first physical quantity calculation device is a cross-sectional area of the subject. The cross section is an effective index with respect to the size of the subject. Another example of the physical quantity with respect to the size of the subject calculated by the first physical quantity calculation device is a volume of the subject. The volume is also an effective index with respect to the size of the subject. It should be noted that the "size of the subject" herein includes an area (extent) or volume.

Furthermore, the physical quantity with respect to the size of the subject calculated by the first physical quantity calculation device is not limited to the cross-sectional area or volume of the subject. It may be an attenuation ratio of the subject. The attenuation ratio of the subject is obtained by counting radiation that is applied from the external radiation source in a state where no subject exists and counting radiation that is applied from the external radiation source through the subject in a state where a subject exists to determine a counting rate thereof. Here, the attenuation ratio of the subject is also an effective index with respect to the size of the subject.

Another embodiment of the foregoing tomographic equipment and the imaging system provided therewith includes a counting device that counts radiation generated from a subject with radiopharmaceutical administered thereto. Physical quantity for evaluating an image that is calculated by the second physical quantity calculation device is a noise equivalent count in accordance with radiation counted by the counting device. The third physical quantity calculation device calculates a noise equivalent count per size of the subject. The noise equivalent count is useful as an index for simply evaluating image quality as noted in the section "BACKGROUND ART." For taking into consideration of the physical quantity with respect to the size of the subject for the noise equivalent count, a noise equivalent count per size of the subject is calculated and determined, whereby the noise equivalent count may be determined that is independent of the physical quantity with respect to the size of the subject.

In the foregoing tomographic equipment and the imaging system provided therewith, an imaging condition setting device may be provided that sets an imaging condition in accordance with physical quantity for evaluating an image per size of the subject calculated by the third physical quantity calculation device. The physical quantity for evaluating the image per size of the subject calculated by the third physical quantity calculation device is independent of the physical quantity with respect to the size of the subject, and is an index for examining a subsequent imaging condition. Accordingly, it is possible to determine an extent of image quality to be secured in the subsequent imaging.

Moreover, the method of acquiring imaging data according this invention is a method of acquiring imaging data by performing coincidence of radiation generated from a subject with radiopharmaceutical administered thereto, and includes a first physical quantity calculating step to calculate physical quantity with respect to a size of the subject, a second physical quantity calculating step to calculate physical quantity for evaluating an image, and a third physical quantity calculating step to evaluate physical quantity for evaluating an image per size of the subject based on the physical quantity calculated in the first physical quantity calculating step and the physical quantity calculated in the second physical quantity calculating step.

According to the method of acquiring the imaging data of this invention, the physical quantity with respect to the size of the subject is calculated in the first physical quantity calculating step, and the physical quantity for evaluating the image is calculated in the second physical quantity calculating step. In the third physical quantity calculating step, the physical quantity for evaluating the image per size of the subject is calculated based on the physical quantity calculated in the first physical quantity calculating step and the physical quantity calculated in the second physical quantity calculating step. Accordingly, the physical quantity for evaluating the image per size of the subject is calculated as noted above, whereby an index may be determined that is independent of physical quantity with respect to the size of the subject in evaluating the image.

In the foregoing method of acquiring imaging data, an imaging condition setting step may be included to set an imaging condition in accordance with the physical quantity for evaluating an image per size of the subject calculated in the third physical quantity calculation step. The physical quantity for evaluating the image per size of the subject calculated in the third physical quantity calculation step is independent of the physical quantity with respect to the size of the subject, and is an index for examining a subsequent imaging condition. Accordingly, it is possible to determine an extent of image quality to be secured in the subsequent imaging.

Moreover, where the imaging condition setting step to set an imaging condition is included, it is preferable to conduct imaging under the imaging condition set in the imaging condition setting step, and thereafter to repeat the first physical quantity calculation step, the second physical quantity calculation step, and the third physical quantity calculation step in accordance with the imaging data acquired in the imaging. Such repeat allows determination of an extent of image quality to be secured in the subsequent imaging with the repeat. Furthermore, it is more preferable that an extent of image quality to be secured in the imaging may be determined through the repeat during a series of imaging.

Effect of the Invention

With the tomographic equipment according to this invention, the imaging system provided therewith, and the method of acquiring imaging data, the physical quantity with respect to a size of the subject is calculated, and the physical quantity for evaluating an image is calculated. The physical quantity for evaluating the image per size of the subject is calculated based on the physical quantity with respect to the size of the subject and the physical quantity for evaluating an image. The physical quantity for evaluating the image per size of the subject is calculated as noted above, whereby an index may be determined that is independent of the physical quantity with respect to the size of the subject in evaluating the image.

DESCRIPTION OF REFERENCES

Figure 1:
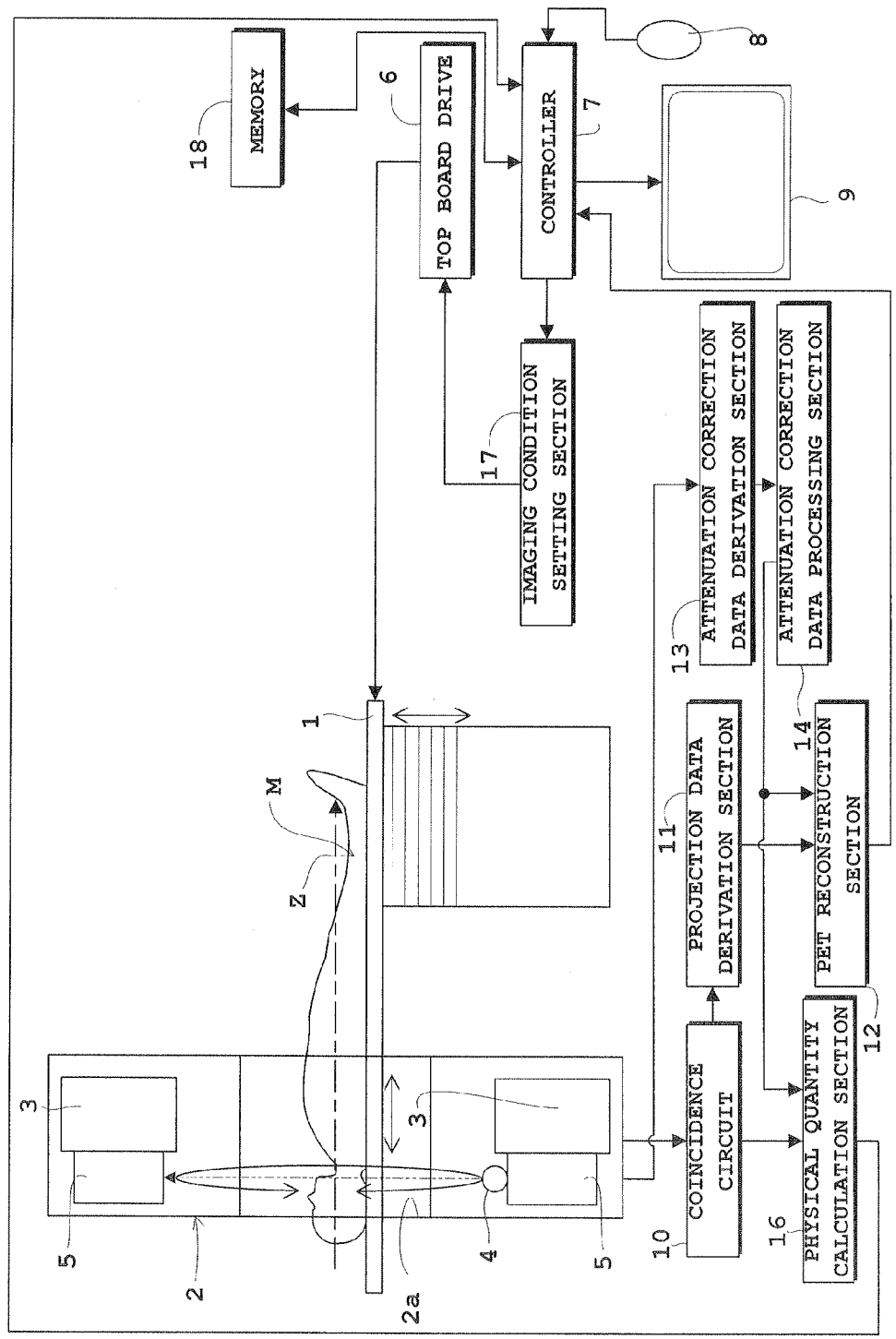
FIG. 1 is a side view and a block diagram of PET (Positron Emission Tomography) equipment according to Embodiment 1.

4 . . . point radiation source
10 . . . coincidence circuit
16b . . . NEC calculation section
16c . . . Cross-sectional area calculation section
16d . . . C-NEC calculation section
17 . . . imaging condition setting section
S . . . cross-section
M . . . subject Embodiment 1

Figure 2:
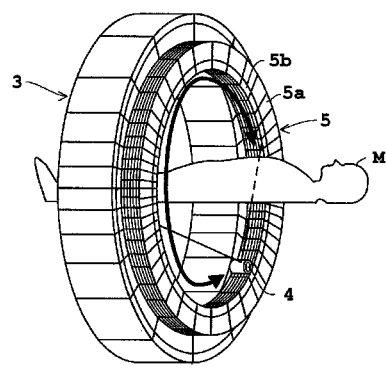
FIG. 2 shows a layout of a gamma-ray detector in the PET equipment.

Embodiment 1 of this invention will be described in detail hereinafter with reference to the drawings. FIG. 1 is a side view and a block diagram of PET (Positron Emission Tomography) equipment according to Embodiment 1. FIG. 2 shows a layout of a gamma-ray detector in the PET equipment.

As shown in FIG. 1, the PET equipment of Embodiment 1 includes a top board 1 that supports a subject M. The top board 1 moves upward and downward, and moves horizontally along a body axis Z of the subject M. With this configuration, the subject M supported on the top board 1 is passed through an opening 2a of a gantry 2, mentioned later, and scanned from the head to the abdomen and legs, in turn, to acquire diagnosis data such as projection data or a sectional image of the subject M.

Besides the top board 1, the PET equipment of Embodiment 1 includes the gantry 2 with the opening 2a and a gamma-ray detector 3 formed of two or more scintillator blocks (not shown) and two or more photomultipliers (not shown) that are arranged adjacent to one another. As shown in FIG. 2, the gamma-ray detector 3 is arranged in a ring shape so as to surround the body axis Z of the subject M, and embedded in the gantry 2. The photomultipliers are coupled to the scintillator blocks. Specific examples of arrangement of the scintillator blocks include an arrangement that two scintillator blocks are located in a direction parallel to the body axis Z of the subject M and many scintillator blocks are located about the body axis Z of the subject M. The gamma-ray detector 3 acquires emission data mentioned later.

In addition, a point radiation source 4 and a gamma-ray detector 5 that acquires attenuation correction data (also called "transmission data"), mentioned later, are included. The gamma-ray detector 5 for attenuation correction data is formed of scintillator blocks 5a (see FIG. 2) and photomultipliers 5b (see FIG. 2), which is similar to the gamma-ray detector 3 for acquiring emission data. The point radiation source 4 is a radiation source that irradiates radiation of a same form as radiopharmaceutical administered to the subject M, i.e., radioisotope (RI) (gamma rays in Embodiment 1), and is arranged outside the subject M. The point source 4 is embedded in the gantry 2. The point radiation source 4 rotates about the body axis Z of the subject M. The point radiation source 4 corresponds to the external radiation source in this invention.

The gamma-ray detector 5 of Embodiment 1 including Embodiment 2 mentioned later is formed such that two or more scintillator blocks 5a and two or more photomultipliers 5b are arranged along the body axis Z of the subject M as shown in FIG. 2, which is similar to the gamma-ray detector 3. Specifically, the gamma-ray detector 5 is formed as a stack of cylindrical detectors in which a row of detectors that are composed of many gamma-ray detectors 3 in a ring shape is arranged in a stack manner also in the direction of the body-axis Z. Here in Embodiment 1, six rows are to be adopted.

Besides, the PET equipment of Embodiment 1 includes a top board drive 6, a controller 7, an input section 8, an output section 9, a coincidence circuit 10, a projection data derivation section 11, a PET reconstruction section 12, an attenuation correction data derivation section 13, an attenuation correction data processing section 14, a physical quantity calculation section 16, an imaging condition setting section 17, and a memory 18. The top board drive 6 is a mechanism that drives the top board 1 so as to move in such manner as mentioned above. The top board drive 6 is formed of a motor, not shown, and the like.

The controller 7 controls each section en block that constitutes the PET equipment according to Embodiment 1. The controller 7 is formed of a central processing unit (CPU) and the like.

The input section 8 transmits data or commands that an operator inputs to the controller 7. The input section 8 is formed of a pointing device represented by such as a mouse, keyboard, joystick, trackball, and touch panel. The output section 9 is formed of a display screen represented by a monitor, and a printer.

The memory 18 is formed of a storage medium represented by such as a ROM (Read-only Memory), and RAM (Random-Access Memory.) In Embodiment 1, diagnosis data processed in the projection data derivation section 11 or PET reconstruction section 12, attenuation correction data determined in the attenuation correction data derivation section 13, attenuation correction data processed in the attenuation correction data processing section 14, a sectional image to which attenuation correction is performed in the PET reconstruction section 12 based on the attenuation correction data, and various physical quantity, mentioned later, that is determined by the physical quantity calculation device 16 are written and stored in a RAM, and are read out from the RAM as required. Programs for various types of nuclear medicine diagnoses are stored in advance in the ROM. The controller 7 executes a program to perform each nuclear medicine diagnosis in accordance with the program.

The projection data derivation section 11, PET reconstruction section 12, attenuation correction data derivation section 13, attenuation correction data processing section 14, physical quantity calculation device 16, and imaging condition setting section 17 may be realized by execution with the controller 7 of a program stored in the ROM as a storage medium represented by the foregoing memory 18 or a command inputted by the pointing device representing the input section 8.

A scintillator block of the gamma-ray detector 3 converts gamma rays generated from the subject M with the radiopharmaceutical administered thereto into light. A photo multiplier of the gamma-ray detector 3 performs opt-electric conversion of the converted light to output it into an electric signal. The electric signal is transmitted into the coincidence circuit 10 as image information (pixel). The coincidence circuit 10 corresponds to the count device of this invention.

Particularly, upon administration of the radiopharmaceutical to the subject M, a positron of positron emission type RI annihilates to generate two gamma rays. The coincidence circuit 10 confirms the position of the scintillator block and incidence timing of gamma rays. Only when gamma rays enter simultaneously into the two scintillator blocks arranged across the subject M in an opposed position to each other, image information transmitted is interpreted to be appropriate data. When gamma rays enter into only one scintillator block, the coincidence circuit 10 handles the gamma rays not as gamma rays generated through annihilation of positron but, as a noise. Image information transmitted is then also interpreted to be a noise, and is rejected.

In fact, although such processes are performed in the coincidence circuit 10, noises cannot be removed completely and noise component remains such as a random or scattered coincidence. The noises are sent with a true coincidence count into the project data derivation section 11 and (the NEC calculation section 16b of) the physical quantity calculation section 16. The projection data derivation section 11 determines image information transmitted from the coincidence circuit 10 as projection data. The PET reconstruction section 12 reconstructs the projection data for obtaining a sectional image. The projection data determined in the projection data derivation portion 11 or the sectional image reconstructed in the PET reconstruction section 12 is also called "emission data."

Here, the point radiation source 4 irradiates the subject M with gamma rays while rotating around the body axis Z of the subject M. The scintillator block 5a of the gamma-ray detector 5 for attenuation correction data converts the applied gamma ray into light. The photomultiplier 5b of the gamma-ray detector 5 performs opt-electric conversion of the converted light to output it into an electric signal. The electric signal is transmitted as image information (pixel) to the attenuation correction data derivation section 13.

Attenuation correction data is determined based on image information transmitted to the attenuation correction data derivation section 13. The attenuation correction data derivation section 13 converts CT projection data, i.e., distribution data of X-ray attenuation coefficient, into the distribution data on a gamma ray attenuation coefficient using calculation that shows a relation between an attenuation coefficient of gamma rays or X-rays and energy thereof. Then, the distribution data on a gamma ray attenuation coefficient is determined as attenuation correction data. The derived attenuation correction data is transmitted to the attenuation correction data processing section 14. The attenuation correction data processing section 14 performs reconstruction. Here, attenuation correction data determined in the attenuation correction data derivation section 13 and attenuation correction data reconstructed in the attenuation correction data processing section 14 are also called "transmission data."

The processed attenuation correction data is transmitted to the PET reconstruction section 12 and (a ratio calculation section 16a and a cross-sectional area calculation section 16c of) the physical quantity calculation section 16. The PET reconstruction section 12 obtains a sectional image taking into consideration of attenuation of gamma rays inside the body of the subject M in accordance with the attenuation correction data, thereby performing attenuation correction to the sectional image. The sectional image with attenuation correction performed thereto is transmitted to the output section 9 via the controller 7.

Figure 3:
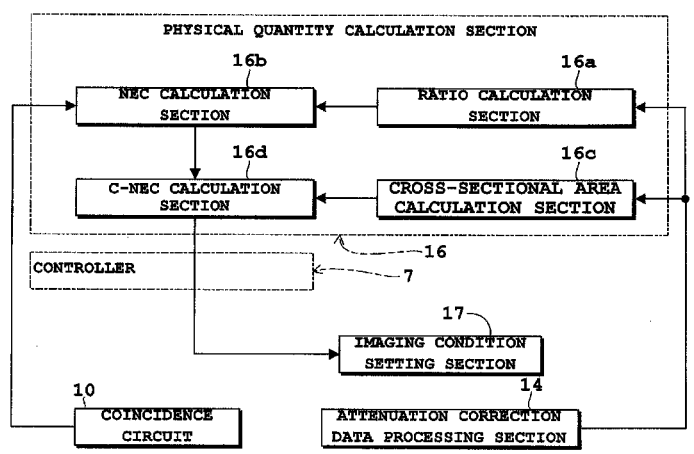
FIG. 3 is a block diagram of a physical quantity calculation section and its peripheral sections.

Next, detailed configuration of the physical quantity calculation section 16 will be described with reference to FIG. 3. FIG. 3 is a block diagram of the physical quantity calculation section and its peripheral sections. The physical quantity calculation section 16 includes a ratio calculation section 16a, an NEC calculation section 16b, a cross-sectional area calculation section 16c, and a C-NEC calculation section 16d. The ratio calculation section 16a calculates a ratio f of the subject M to the gantry 2 based on the attenuation correction data reconstructed in the attenuation correction data processing section 14. The NEC calculation section 16b calculates a noise equivalent count in accordance with data of gamma rays (image information) of which coincidence is performed in the coincidence circuit 10 and that contains random or scattered coincidence. The cross-sectional area calculating section 16c calculates a cross-sectional area of the subject M based on attenuation correction data reconstructed in the attenuation correction data processing section 14. The C-NEC calculation section 16d divides a noise equivalent count NEC calculated in the NEC calculation section 16b by the cross-sectional area of the subject M calculated in the cross-sectional area calculation section 16c, whereby a noise equivalent count per unit area (C-NEC: Cross Section NEC) is calculated. The NEC calculation section 16b corresponds to the second physical quantity calculation device in this invention. The cross-sectional area calculation section 16c corresponds to the first physical quantity calculation device in this invention. The C-NEC calculation section 16d corresponds to the third physical quantity calculation device in this invention. The cross-sectional area of the subject M corresponds to the physical quantity with respect to the size of the subject in this invention. The noise equivalent count NEC corresponds to the physical quantity for evaluating the image in this invention. The noise equivalent count per unit area C-NEC corresponds to the physical quantity for evaluating the image per size of the subject in this invention.

Figure 4:
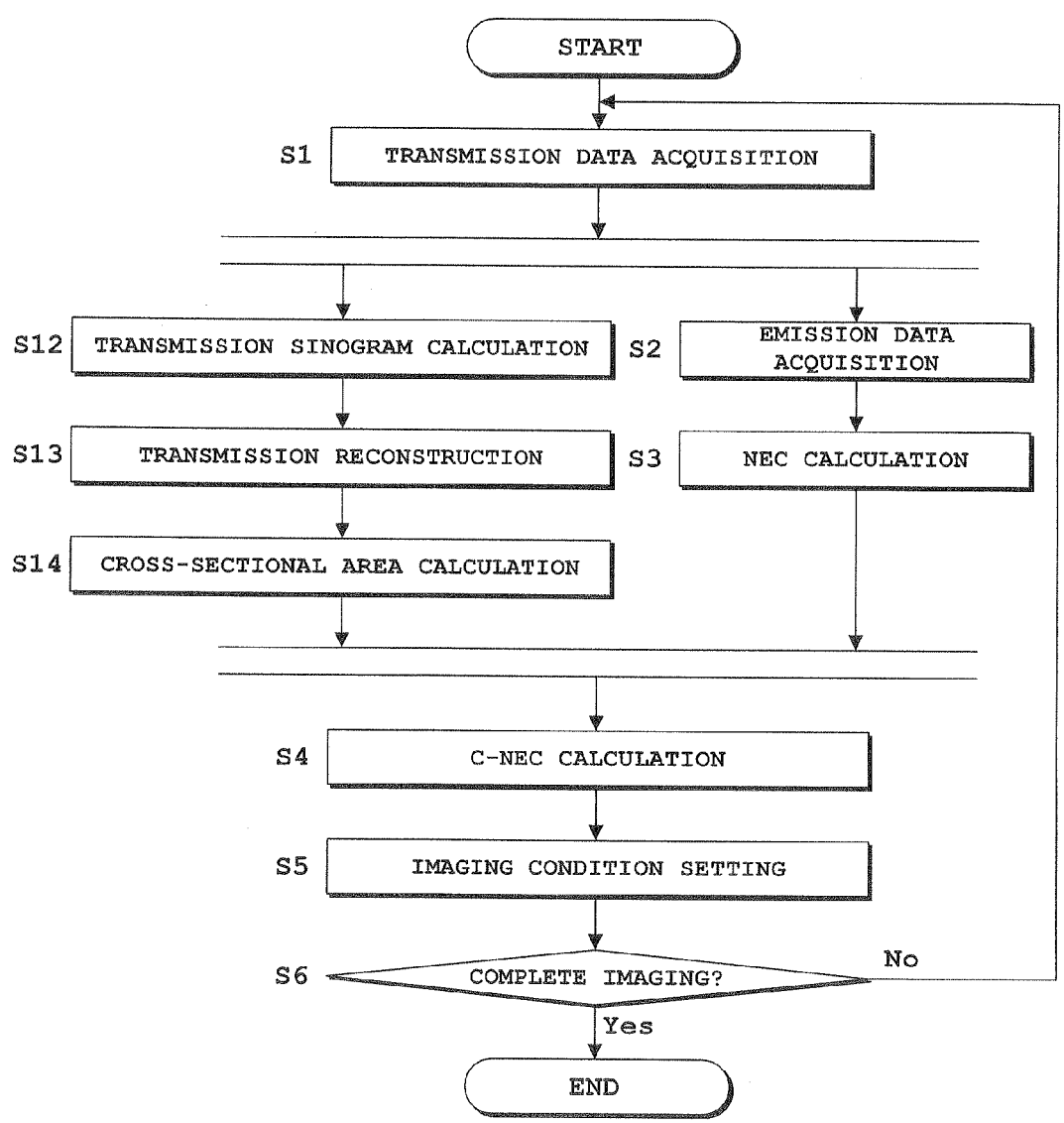
FIG. 4 is a flow chart of a series of imaging data acquisition.
Figure 5:
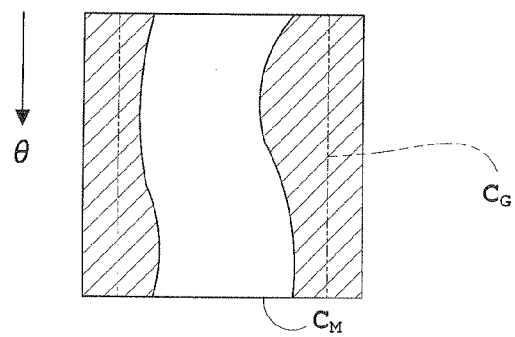
FIG. 5 is a schematic view of sinogram of transmission data.
Figure 6:
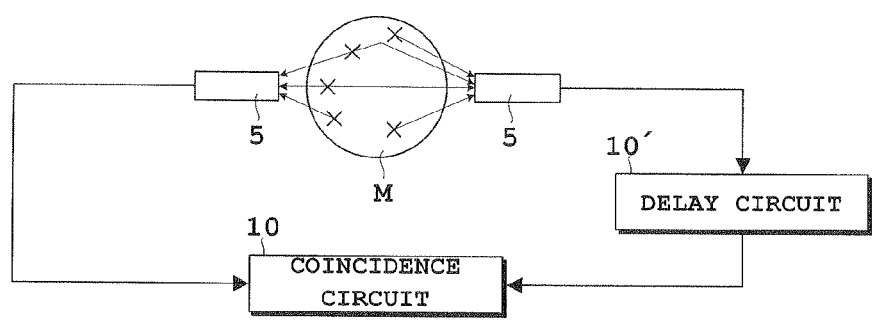
FIG. 6 is a block diagram of a circuit (a delayed coincidence circuit) as a combination of a coincidence circuit and a delay circuit.
Figure 7:
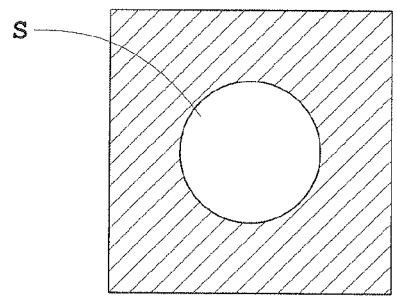
FIG. 7 is a schematic view of a cross section.
Figure 8:
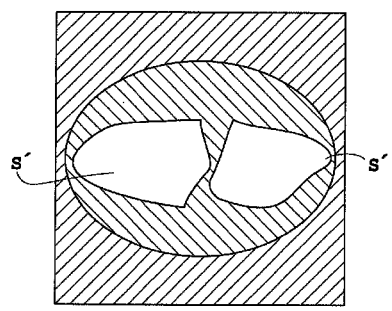
FIG. 8 is a schematic view of the cross section in consideration of a soft tissue.
Figure 9:
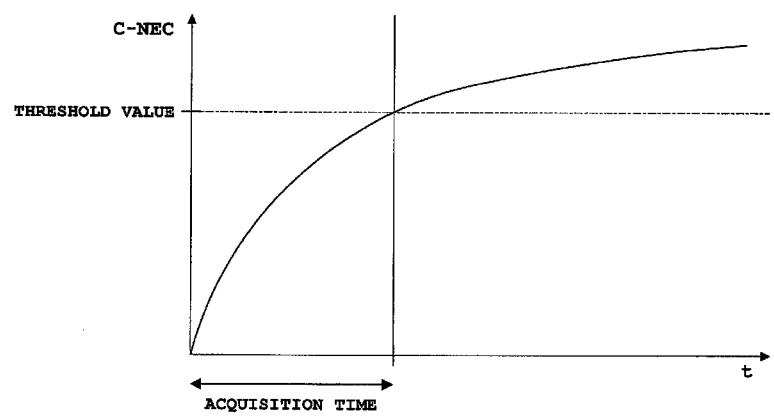
FIG. 9 is a diagram exemplarily showing imaging time and a noise equivalent count per unit area at the time of static data acquisition.

Subsequently, description will be given to detailed processes of a series of imaging data acquisition with reference to FIGS. 4 to 8. FIG. 4 is a flow chart of a series of imaging data acquisition. FIG. 5 is a schematic view of sinogram of transmission data. FIG. 6 is a block diagram of a circuit (delayed coincidence circuit) as a combination of a coincidence circuit and a delay circuit. FIG. 7 is a schematic view of a cross section. FIG. 8 is a schematic view of the cross section in consideration of a soft tissue. FIG. 9 is a diagram exemplarily showing imaging time and a noise equivalent count per unit area at the time of static data acquisition.

Here, explanation will be made in a flow chart of FIG. 4, supposing that (1) the gamma-ray detector 5 detects gamma rays that are applied from the point radiation source 4 through the subject M while the subject M is scanned from the legs, abdomen and head to acquire transmission data, and the gamma-ray detector 3 detects gamma rays generated from the subject M with radiopharmaceutical administered thereto to acquire emission data (such data acquisition in (1) is called "whole-body acquisition"), or (2) the gamma-ray detector 5 detects gamma ray applied to a given region from the point radiation source 4 and transmitted through the subject M to acquire transmission data, and thereafter the gamma-ray detector 3 detects gamma rays generated from the subject M with radiopharmaceutical administered thereto on the same region to acquire emission data (such data acquisition in (2) is called "static data acquisition".) In addition, as shown in FIGS. 1 and 2, the gamma-ray detector 3 for emission is arranged closer to the legs than the gamma-ray detector 5 for transmission (for attenuation correction data.) Consequently, in the whole-body acquisition, transmission data on the same region is previously acquired, and subsequently emission data is acquired.

(STEP 1) Transmission Data Acquisition

The gamma-ray detector 5 for transmission acquires transmission data. Specifically, the scintillator block 5a converts into light gamma rays applied from the point radiation source 4 through the subject M. The photomultiplier 5b performs opt-electric conversion of the converted light to output it into an electric signal. Consequently, the gamma-ray detector 5 detects gamma rays. The electric signal is transmitted to the attenuation correction data derivation section 13 as image information (pixel).

(STEP S2) Emission Data Acquisition

The gamma-ray detector 3 for emission acquires emission data on the same region where transmission data acquisition was performed in STEP S1. Specifically, the scintillator block converts into light gamma rays generated from the subject M with radiopharmaceutical administered thereto. The photomultiplier performs opt-electric conversion of the converted light to output it into an electric signal. Consequently, the gamma-ray detector 3 detects gamma rays. The electric signal is transmitted to the coincidence circuit 10 as image information (pixel). Only when gamma rays containing random and scatter coincidence counts enter simultaneously into the two scintillator blocks arranged across the subject M in an opposed position to each other, the coincidence circuit 10 interprets that image information transmitted is appropriate data. The image information is sent into the projection data derivation section 11. Moreover, the total of the image information in every second is derived as counting rate information (the number of image information per unit time), and is transmitted to the NEC calculation section 16b in the physical quantity calculation section 16.

(STEP S12) Transmission Sinogram Calculation

In parallel with STEP S2, the attenuation correction data derivation section 13 determines attenuation correction data based on the image information transmitted in STEP S1. Specifically, as shown in FIG. 5, let a longitudinal axis be a gamma-ray applying direction θ. Sinogram is to be created having a horizontal axis as a surface direction perpendicular to the body axis Z of the subject M. The derived attenuation correction data (herein the sinogram) is transmitted into the attenuation correction data processing section 14. A portion corresponding to the subject M is illustrated by $C_M$ in FIG. 5. Moreover, a portion corresponding to the gantry 2 is illustrated by $C_G$ in FIG. 5.

(STEP S13) Transmission Reconstruction

The attenuation correction data processing section 14 performs reconstruction to the attenuation correction data (herein the sinogram) transmitted in STEP S12. Among transmission data such as the sinogram processed as mentioned above or the reconstructed attenuation correction data, the sinogram determined in the attenuation correction data derivation section 13 is transmitted into the ratio calculation section 16a in the physical quantity calculation section 16. The attenuation correction data to which the attenuation correction data processing section 14 performs reconstruction is sent into the PET reconstruction section 12 and the cross-sectional area calculation section 16c in the physical quantity calculation section 16.

(STEP S3) NEC Calculation

The projection data derivation section 11 determines the image information transmitted in STEP S2 as projection data. The projection data and the attenuation correction data derived in attenuation correction data processing section 14 in STEP S13 are transmitted into the PET reconstruction section 12. The PET reconstruction section 12 determines a sectional image in consideration of attenuation of gamma rays inside the body of the subject M. Nuclear medicine diagnosis is to be conducted based on the sectional image to which attenuation correction is performed. On the other hand, the NEC calculation section 16b calculates a noise equivalent count NEC using true coincidence count (T), random coincidence count (R), and scattered coincidence count (S) of which the coincidence circuit 10 performs coincidence based on the image information transmitted in STEP S2. The noise equivalent count NEC may be calculated using the foregoing equation (1) or (2). Here in Embodiment 1, the noise equivalent count NEC is to be calculated using the following equation (3).

$$NEC=(T+S)^2/(T+S+2\times f\times R) \tag{3}$$

The actual coincidence circuit 10 derives all of the coincidence counts (T+S+R) and delayed coincidence count (R). Consequently, it is difficult to distinguish between the true coincidence count (T) and scattered coincidence count (S). Assumption that (all the numbers of coincidence counts)−(delayed coincidence count)=(T+S) and is substituted into the foregoing equation (3). The delayed coincidence count is directly substituted into the random coincidence count (R). As shown in FIG. 6, the delay circuit 10' is combined with the coincidence circuit 10. As a result, time delay occurs to gamma rays originally out of a time window with the delay circuit 10'. The inputted time difference of gamma rays stays within the time window with the delay circuit 10'. Consequently, the delay coincidence count is determined as a component of which coincidence is performed in the coincident circuit 10. The gamma ray of which coincidence was performed in the coincidence circuit 10 by the delay circuit 10' is distinguishable as random coincidence (R) since the gamma ray is a noise out of the time window if no delay circuit 10' is present.

Here, f in the foregoing equation (3) is a ratio f of the subject M to the gantry 2. The ratio f may be calculated based on sinogram determined with the attenuation correction data derivation section 13 in STEP S12. It is possible to determine the ratio f from areas of $C_G$ and $C_M$ in FIG. 5. The ratio f may also be determined from the attenuation correction data reconstructed in the attenuation correction data processing section 14 in STEP S13. The ratio f determined in such manner is sent into the NEC calculation section 16b to be substituted into the foregoing equation (3). The true coincidence count (T), random coincidence count (R), and scattered coincidence count (S) of which coincidence was performed in the coincidence circuit 10 are substituted into the foregoing equation (3). Consequently, the noise equivalent count NEC is to be calculated. The calculated noise equivalent count NEC is sent into the C-NEC calculation section 16d. The STEP S3 corresponds to the second physical quantity calculation step in this invention.

Here, the noise equivalent count NEC indicates true coincidence count (T) that apparently corresponds to the noise of an image obtained when no random coincidence count (R) or scattered coincidence count (S) is present. The noise equivalent count NEC is not limited in the foregoing equation (1), equation (2), or equation (3). Moreover, a counted value to be counted (count value) depends on a dose of radiation, and a size of the subject M is not considered. Now, a noise equivalent count per unit area C-NEC is to be calculated as in STEP S4 mentioned later.

(STEP S14) Cross-Sectional Area Calculation

The cross-sectional area calculating section 16c calculates a cross-sectional area of the subject M based on the attenuation correction data reconstructed in the attenuation correction data processing section 14 in STEP S13. As shown in FIG. 7, a cross-sectional area S of the subject M having a surface perpendicular to the body axis Z of the subject M as a cross-section is to be calculated from the reconstructed attenuation correction data (attenuation coefficient map.) The calculated cross-sectional area S is sent into the C-NEC calculation section 16d. When the cross-sectional area S is calculated, a soft tissue may be considered as shown in FIG. 8. For instance, in the case of a lung, there exists gas (e.g., air) other than the soft tissue, and an attenuation of gamma rays is low. Accordingly, only the cross-sectional area S' of the soft tissue in the lung may be considered. Weighting may be performed to the cross-sectional area S in accordance with attenuation. Reduced weighting may be performed to a portion with lower attenuation to multiply the cross-sectional area of the portion by the reduced weighting. Enhanced weighting may be performed to a portion with higher attenuation to multiply the cross-sectional area of the portion by the enhanced weighting. The STEP S14 corresponds to the first physical quantity calculation step in this invention.

(STEP S4) C-NEC Calculation

The noise equivalent count NEC calculated in the NEC calculation section 16b in STEP S3 is divided by the cross-sectional area S calculated in the cross-sectional area calculation section 16c in STEP S14, as the following equation (4). The C-NEC calculation section 16d calculates noise equivalent count C-NEC per unit area.

$$C\text{-}NEC = NEC/\text{Cross Section} \quad (4)$$
$$= \{(T+S)^2/(T+S+2\times f \times R)\}/\text{Cross Section}$$

Where, "Cross Section" in the foregoing equation (4) is a value of cross-sectional area S. The STEP S4 corresponds to the third physical quantity calculation step in this invention.

(STEP S5) Imaging Condition Setting

The noise equivalent count per unit area C-NEC calculated in the C-NEC calculation section 16d in STEP S4 is sent into the imaging condition setting section 17 via the controller 7 (see FIG. 3.) The imaging condition setting section 17 sets an imaging condition based on the sent noise equivalent count per unit area C-NEC. In Embodiment 1, the imaging condition setting section 17 controls the top board drive 6 (see FIG. 1) for controlling traveling speed of the top board 1 or downtime of the top board 1. Therefore, the traveling speed or downtime of the top board 1 in Embodiment 1 corresponds to the imaging condition in this invention. Moreover, the imaging condition setting section 17 corresponds to the imaging condition setting device in this invention.

In both of the whole-body acquisition (1) and the static data acquisition (2) mentioned above, the noise equivalent count per unit area C-NEC that has no effect on image quality is set in advance as a threshold value. In the whole-body acquisition, where the noise equivalent count per unit area C-NEC calculated in STEP S5 is higher than the threshold value set in advance, the traveling speed of the top board 1 is accelerated such that the data acquisition time may be reduced. Where the noise equivalent count per unit area C-NEC calculated in STEP S5 is lower than the threshold value set in advance, the traveling speed of top board 1 is slowed down such that the data acquisition time may extend. In the static data acquisition, as shown in FIG. 9, as the downtime of the top board 1 (that is, imaging time (data acquisition time) in the case of the static data acquisition) becomes longer, counted gamma rays (herein image information) increase due to accumulation over time. Accordingly, the noise equivalent count C-NEC per unit area also increases. Imaging is to be completed when the noise equivalent count per unit area C-NEC that increases over time is higher than the threshold value set in advance. The STEP S5 corresponds to the imaging condition setting step in this invention.

(STEP S6) Complete Imaging?

In the whole-body acquisition, it is determined whether or not to reach a scanning region. Where the scanning region is not reached, imaging is not considered completed, thereby returning to STEP 1 to repeat STEPs S1 to S6. Where the scanning region is reached, imaging is considered completed, and a series of processes is to be completed (FIG. 4 is a flow chart in the whole-body acquisition.) In the static data acquisition, it is determined whether or not to reach the downtime (imaging time) of the top board 1 that is set based on the noise equivalent count per unit area C-NEC in STEP S5. Then, a process is on standby at STEP S6 until the time is reached to execute looping. Where the time is reached, imaging is considered completed, and a series of processes is to be completed.

According to the PET equipment concerning Embodiment 1 with the foregoing configuration, the PET equipment includes the cross-sectional area calculation section 16c, the NEC calculation section 16b, and the C-NEC calculation section 16d. The cross-sectional area calculation section 16c calculates a cross-sectional area of the subject M as physical quantity with respect to a size of the subject M, and the NEC calculation section 16b calculates a noise equivalent count NEC as physical quantity for evaluating an image. The C-NEC calculation section 16d calculates a noise equivalent count per unit area C-NEC as physical quantity for evaluating an image per size of the subject M in accordance with the cross-sectional area of the subject M calculated in the cross-sectional area calculation section 16c and the noise equivalent count NEC calculated in the NEC calculation section 16b. Accordingly, the noise equivalent count per unit area C-NEC is calculated as noted above, whereby an index may be determined that is independent of the cross-sectional area of the subject M in evaluating the image.

In Embodiment 1, the PET equipment includes the point radiation source 4 that externally irradiates the subject M with radiation of a same form as radiopharmaceutical. The cross-sectional area calculation section 16c calculates physical quantity with respect to a size of the subject M (a cross-sectional area in Embodiment 1) based on gamma rays that are applied from the point radiation source 4 and transmitted through the subject. Data (transmission data in Embodiment 1) acquired based on gamma rays that are applied from the point radiation source 4 as the external radiation source and transmitted through the subject has form information on the subject M. Consequently, the cross-sectional area calculation section 16c may simply calculate the physical quantity with respect to the size of the subject M (cross-sectional area in Embodiment 1) in accordance with the gamma rays.

Moreover, in Embodiment 1, the cross-sectional area of the subject M is described as an example of physical quantity with respect to the size of the subject M that is calculated in the first physical quantity calculation device in this invention (the cross-sectional area calculation section 16c in Embodiment 1.) The cross section is an effective index with respect to the size of the subject M.

Moreover, in Embodiment 1, the coincidence circuit count circuit 10 is provided that counts gamma rays generated from the subject with radiopharmaceutical administered thereto. The physical quantity for evaluating an image that is calculated in the second physical quantity calculation device in this invention (the NEC calculation section 16b in Embodiment 1) corresponds to the noise equivalent count NEC based on gamma rays that is counted in the coincidence circuit 10. The third physical quantity calculation device in this invention (the C-NEC calculation section 16d in Embodiment 1) calculates the noise equivalent count per size of the subject M (per unit area in Embodiment 1) C-NEC. The noise equivalent count NEC is useful as an index for simply evaluating image quality as noted in the section "BACKGROUND ART." For taking into consideration of the physical quantity with respect to the size of the subject M (cross-sectional area in Embodiment 1) for the noise equivalent count, a noise equivalent count per size of the subject M (per unit area in Embodiment 1) C-NEC is calculated and determined, whereby the noise equivalent count C-NEC may be determined that is independent of the physical quantity with respect to the size of the subject M (cross-sectional area).

Moreover, in Embodiment 1, the imaging condition setting section 17 is provided that sets an imaging condition based on the noise equivalent count per unit area C-NEC calculated by the C-NEC calculated section 16d. The noise equivalent count per unit area C-NEC calculated by the C-NEC calculation section 16d is independent of the cross-sectional area of the subject M, and is an index for examining a subsequent imaging condition. Accordingly, it is possible to determine an extent of image quality to be secured in the subsequent imaging.

Moreover, especially in the whole-body acquisition in Embodiment 1, imaging is conducted under an imaging condition set in STEP S5. Thereafter, STEPs S1 to S6 including STEPs S3, S14, and S4 are to be repeated based on imaging data acquired through the imaging. Such repeat allows determination of an extent of image quality to be secured in the subsequent imaging with the repeat. Furthermore, an extent of image quality to be secured in the imaging may be determined through the repeat during a series of imaging. Here in static data acquisition, STEPs S1 to S6 may be repeated. Repeating in the static data acquisition allows updating of downtime (imaging time) of the top board to the latest one. Accordingly, an extent of image quality to be secured during imaging may be determined.

Embodiment 2

Figure 10:
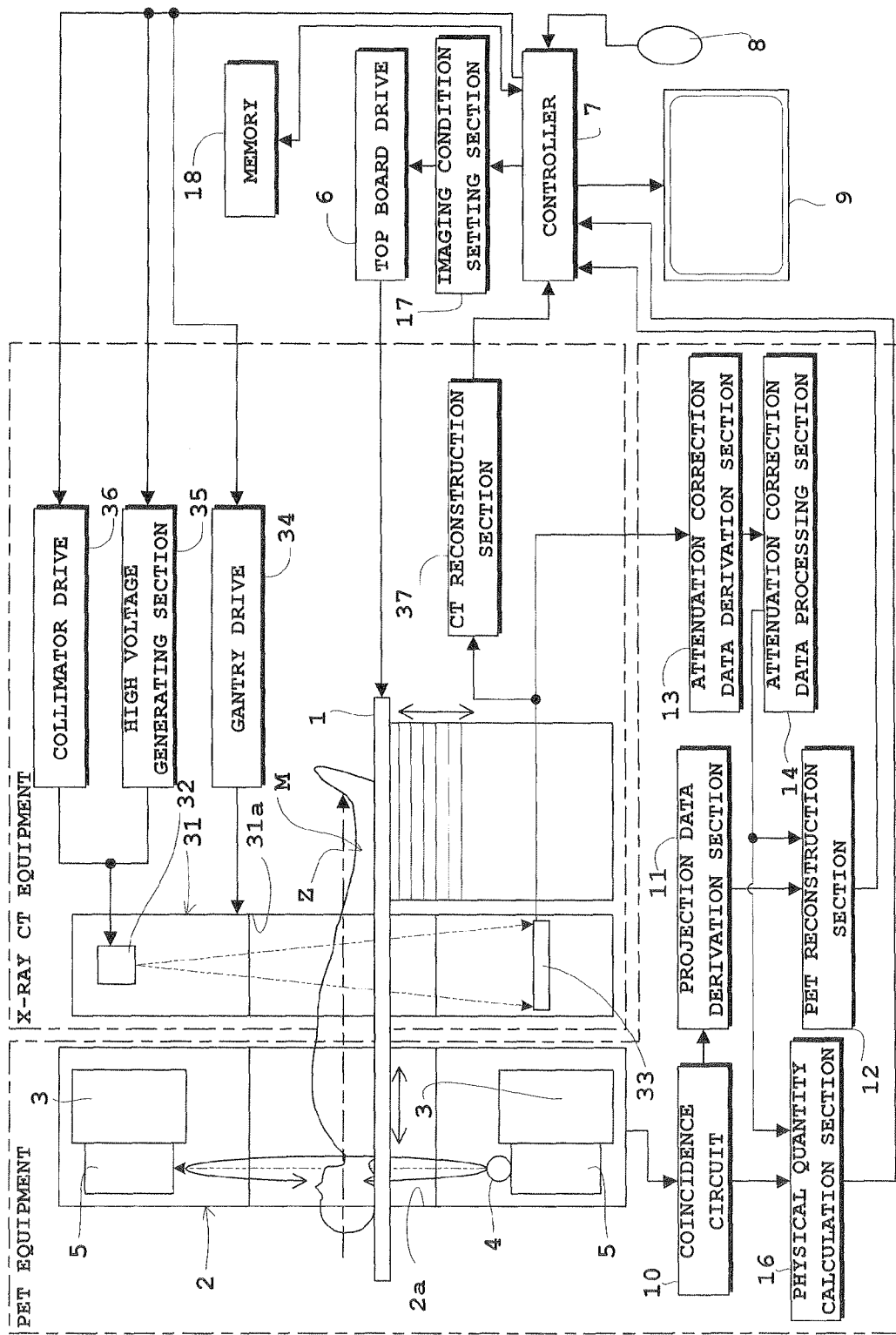
FIG. 10 is a side view and a block diagram of an imaging system according to Embodiment 2 having PET equipment and X-ray CT equipment.

Next, Embodiment 2 of this invention will be described in detail hereinafter with reference to the drawings. FIG. 10 is a side view and a block diagram of an imaging system according to Embodiment 2 having PET equipment and X-ray CT equipment. The X-ray CT equipment corresponds to the imaging equipment in this invention.

In the foregoing Embodiment 1, the PET equipment 4 includes the point radiation source 4. The point radiation source 4 irradiates the subject M with gamma rays of a same form as radiopharmaceutical. The gamma-ray detector 5 detects the gamma rays. Consequently, attenuation correction data is determined as form information based on the radiation. Here in Embodiment 2, CT projection data is to be used as the attenuation correction data. The attenuation correction data corresponds to the CT image in this invention.

The X-ray CT equipment includes a gantry 31 with an opening 31a, an X-ray tube 32, and an X-ray detector 33. The X-ray tube 32 and X-ray detector 33 are arranged across the subject M in an opposed position to each other, and are embedded in the gantry 31. Many detecting elements constituting the X-ray detector 33 are disposed about the body axis Z of the subject M in a fan shape.

In addition, the X-ray CT equipment includes a gantry drive 34, a high voltage generating section 35, a collimator drive 36, and a CT reconstruction section 37. The CT reconstruction section 37 may be realized by execution with the controller 7 of a program stored in the ROM as a storage medium represented by the memory 18 mentioned above or a command that is inputted by the input section 8. Here, the CT projection data mentioned later, and the CT sectional images processed by the CT reconstruction section 37 are written and stored in a RAM of the memory 18 as in the foregoing Embodiment 1 and are read out from the RAM as required. The CT projection data and the CT sectional images for CT correspond to the CT image in this invention.

The gantry drive 34 is a mechanism for rotating the X-ray tube 32 and the X-ray tube detector 33 about the body axis Z of the subject M within the gantry 21 while maintaining a relationship facing to each other. The gantry drive 34 is formed of a motor etc., not shown.

A high voltage generating section 35 generates a tube voltage and a tube current in the X-ray tube 32. The collimator drive 36 sets an X-ray irradiation visual field, and moves the collimator (not shown) adjacent to the X-ray tube 32 in a horizontal direction. The collimator drive 36 is formed of a motor etc., not shown.

In the case of an indirect conversion type X-ray detector 33, a scintillator (not shown) in the X-ray detector 33 converts an X-rays applied from the X-ray tube 32 and transmitted through the subject M into a light, and a photosensitive film (not shown) performs opt-electric conversion of the converted light to output it into an electric signal. In the case of a direct conversion type X-ray detector 33, a radiation sensitive film (not shown) directly converts an X-ray into an electric signal for output. The electric signal is then sent into the CT reconstruction section 37 as image information (pixel.) The image information sent into the CT reconstruction section 37 is then transmitted as CT projection data.

The CT projection data has form information as in the attenuation correction data in Embodiment 1. Here in Embodiment 2, the CT projection data is sent into the attenuation correction data derivation section 13 for use as attenuation correction data, and simultaneously sent into the CT reconstruction section 37. The image information (CT projection data) sent into the CT reconstruction section 37 is reconstructed to obtain a CT sectional image. The CT sectional image is sent to the output section 9 via the controller 7. Each function of the processing section at a subsequent stage of the PET equipment containing the attenuation correction data derivation section 13 (the attenuation correction section 14 and the physical quantity calculation section 16) are the same as those in Embodiment 1. Thus, descriptions thereof will be omitted. The PET sectional image that the reconstruction section 12 reconstructs and performs attenuation correction thereto and the CT sectional image that the CT reconstruction section 37 reconstructs may be outputted in a superimposed condition with the output section 9.

Accordingly, in Embodiment 2, the CT projection data detected and obtained by the X-ray detector 33 in the X-ray CT equipment is sent into the CT reconstruction section 37 and the attenuation correction data derivation section 13 for use the CT projection data as the attenuation correction data.

Similar to Embodiment 1, with an imaging system in the PET-CT equipment according to Embodiment 2 having the foregoing construction, the cross-sectional area of the subject M is calculated as physical quantity with respect to the size of the subject M. The noise equivalent count NEC is calculated as physical quantity for evaluating an image. The noise equivalent count per unit area C-NEC is calculated as physical quantity for evaluating an image per size of the subject M in accordance with the cross-sectional area of the subject M and the noise equivalent count NEC. Accordingly, the noise equivalent count per unit area C-NEC is calculated as noted above, whereby an index may be determined that is independent of the cross-sectional area of the subject M in evaluating the image.

In Embodiment 2, the first physical quantity calculation device in this invention (the cross-sectional area calculation section 16c in Embodiment 2) calculates physical quantity with respect to the size of the subject M (the cross-sectional area of the subject M in Embodiment 2) based on form information on the subject M (CT projection data used as the attenuation correction data in Embodiment 2) acquired with the imaging equipment in this invention (the X-ray CT equipment in Embodiment 2.) Since data acquired from the imaging equipment (X-ray CT equipment in Embodiment 2) is form information on the subject M, the first physical quantity calculation device (the cross-sectional area calculation section 16c in Embodiment 2) may simply calculate the physical quantity with respect to the size of the subject (cross-sectional area in Embodiment 2) in accordance with the form information.

Here in Embodiment 2, calculation is to be performed as follows when the imaging equipment in this invention is X-ray CT equipment, and when the first physical quantity calculation device in this invention (the cross-sectional area calculation section 16c in Embodiment 2) calculates the physical quantity with respect to the size of the subject M (cross-sectional area in Embodiment 2) in accordance with the form information on the subject M (CT image, i.e. CT projection data used as the attenuation correction data in Embodiment 2.) Specifically, the X-ray CT equipment obtains a CT image, and thus the CT image has form information. The first physical quantity calculation device (cross-sectional area calculation section 16c in Embodiment 2) calculates the physical quantity with respect to the size of the subject M (cross-sectional area in Embodiment 2) in accordance with the CT image.

Here in Embodiment 2, the PET equipment and the X-ray CT equipment are integrated into one imaging system. The X-ray CT equipment may be formed as an external equipment of the PET equipment and the form information of the subject M (CT projection data used as the attenuation correction data in Embodiment 2) acquired from the X-ray CT equipment may be transferred to the PET equipment. In this case, the X-ray CT equipment is external equipment seen from the PET equipment. Consequently, the X-ray CT equipment corresponds to the external equipment in this invention.

This invention is not limited to the foregoing embodiments, but may be modified as follows.

(1) In each of the foregoing embodiments, description has been given to the PET equipment as one example. This invention is not limited to the PET equipment and applicable to tomographic equipment for performing coincidence of radiation generated from a subject with radiopharmaceutical administered thereto to obtain a sectional image.

(2) Each of the foregoing embodiments includes static type equipment in which the gamma-ray detector 5 for transmission detects gamma rays under a static condition. The equipment may be a rotating type in which the gamma-ray detector 5 detects gamma rays while rotating about the subject M.

(3) In the foregoing Embodiment 2, the imaging equipment in this invention is X-ray CT equipment. The first physical quantity calculation device in this invention (the cross-sectional area calculation section 16c in Embodiment 2) calculates the physical quantity with respect to the size of the subject M (cross-sectional area in Embodiment 2) in accordance with the form information on the subject M (CT image, i.e. CT projection data used as the attenuation correction data in Embodiment 2.) The imaging equipment is not limited to the X-ray CT equipment as in Embodiment 2. Moreover, the form information is not limited to the CT image. The equipment is applicable that obtains a given image through predetermined imaging to the subject M and data acquired with the equipment has form information. For instance, an image obtained by nuclear magnetic resonance imaging (MRI: Magnetic Resonance Imaging) equipment has form information. Consequently, the first physical quantity calculation device (cross-sectional area calculation section 16c in Embodiment 2) may calculate the physical quantity with respect to the size of the subject (cross-sectional area in Embodiment 2) in accordance with the form information obtained from the MRI equipment.

(4) In each of the foregoing embodiments, data as a basis for calculating the physical quantity with respect to the size of the subject M (cross-sectional area in each embodiment) with the first physical quantity calculation device (cross-sectional area calculation section 16c in each embodiment) is form information on the subject M (transmission data in Embodiment 1, and CT image, i.e., CT projection data used as the attenuation correction data in Embodiment 2.) Such data is not limited to the form information on the subject M as in each embodiment. Even when data is functional information on the subject M (for instance, emission data), it is possible to calculate the physical quantity with respect to the size of the subject since a distribution of radioactivity in the subject that spreads with the radiopharmaceutical may show a contour of the subject.

(5) In each of the foregoing embodiments, the cross-sectional area of the subject M is described as an example of physical quantity with respect to the size of the subject M that is calculated in the first physical quantity calculation device in this invention (the cross-sectional area calculation section 16c in each embodiment.) Such physical quantity is not limited to the cross-sectional area as in each embodiment. The "size of the subject" herein includes an area (extent) or volume as mentioned above. Thus, the volume may be adopted as the size of the subject M. Consequently, the physical quantity for evaluating the image calculated by the second physical quantity calculation section (the NEC calculation section 16b in each embodiment) is divided by the volume, whereby the noise equivalent count per unit volume may be determined.

Here, let the length of the subject M in the body axis Z direction be L. The noise equivalent count NEC is divided by L to obtain the noise equivalent count normalized by L (i.e., noise equivalent count per unit length.) This may be used as an index. Assuming that the noise equivalent count normalized by L be NEC'. The NEC' is given by the following equation (5).

$$NEC'=NEC/L \tag{5}$$

Here, the NEC obtained from the foregoing equation (1) or (2) may be substituted for the right-hand side of the foregoing equation (5) for determining the noise equivalent count NEC' normalized by L. The NEC obtained from the foregoing equation (3) may be substituted for the right-hand side of the foregoing equation (5) for determining the noise equivalent count NEC' normalized by L. Where the NEC obtained from the foregoing equation (3) is substituted for the right-hand side of the foregoing equation (5), the noise equivalent count NEC' normalized by L is given by the following equation (6).

$$NEC'=(T+S)^2/(T+S+2 \times f \times R) \times 1/L \tag{6}$$

The noise equivalent count NEC' normalized by L with the foregoing equation (6) is divided by the cross-section area S for determining a noise equivalent count per unit area normalized by L. Assuming that the noise equivalent count per unit area normalized by L be C-NEC'. The noise equivalent count per unit area C-NEC' normalized by L is given by the following equation (7).

$$C\text{-}NEC' = NEC'/\text{Cross Section} \quad (7)$$
$$= NEC/(\text{Cross Section} \times L)$$
$$= (T+S)^2/(T+S+2 \times f \times R) \times$$
$$1/(\text{Cross Section} \times L)$$

Where, the "Cross Section" in the foregoing equation (7) is a value of cross-sectional area S as mentioned above. Thus, Cross Section×L is a value of multiplication of the cross-sectional area S by the length L, i.e., a volume. For determining the noise equivalent count per unit area C-NEC' normalized by L, the noise equivalent count NEC' is divided by the volume (Cross-section×L) to obtain the noise equivalent count per unit volume. The volume is also an effective index with respect to the size of the subject M.

(6) In each of the foregoing embodiments, the cross-sectional area of the subject M is described as an example of physical quantity with respect to the size of the subject M that is calculated in the first physical quantity calculation device in this invention (cross-sectional area calculation section 16c in each embodiment.) Such physical quantity is not limited to the cross-sectional area as in each embodiment or the volume as in modification (5). It may be an attenuation ratio of the subject. The attenuation ratio of the subject is obtained by counting radiation that is applied from the external radiation source in a state where no subject exists and counting radiation that is applied from the external radiation source (the point radiation source 4 in Embodiment 1) through the subject in a state where a subject exists to determine a counting rate thereof. Here, the attenuation ratio of the subject is also an effective index with respect to the size of the subject.

(7) In each of the foregoing embodiments, the noise equivalent count NEC is described as an example of physical quantity for evaluating an image that is calculated in the second physical quantity calculation device in this invention (NEC calculation section 16b in each embodiment.) In addition, the noise equivalent count per unit area C-NEC is described as an example of physical quantity for evaluating an image per size of the subject M that is calculated in the third physical quantity calculation device in this invention (the C-NEC calculation section 16d in each embodiment.) Such physical quantity is not limited to the noise equivalent count as in each embodiment. It is not particularly limited as long as it is the physical quantity for evaluating an image. For instance, the ratio (R/(T+S+R)) of the random coincidence count (R) to the total coincidence counts including the true coincidence count (T), the random coincidence count (R), and the scattered coincidence count (S) may be physical quantity for evaluating an image noise. Thus, R/(T+S+R) per size of the subject may be determined as the physical quantity for evaluating an image.

Figure 11:
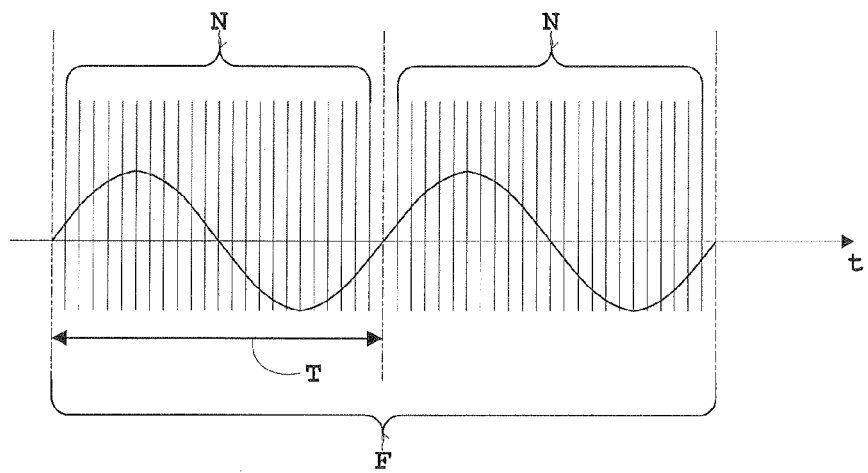
FIG. 11 is a timing chart used with explanation of conducting imaging in synchronization with cardiac muscle contraction.
Figure 12:
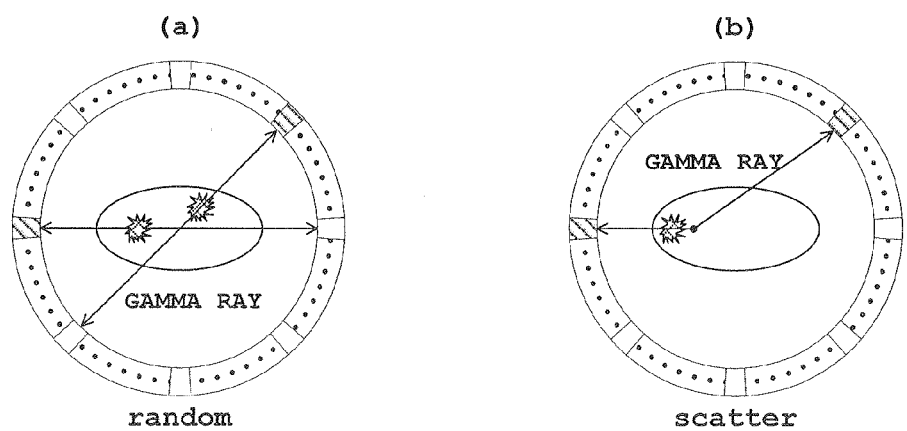
FIG. 12(a) is a schematic view exemplarily showing a state of a random coincidence.
FIG. 12(b) is a schematic view exemplarily showing a state of a scatter coincidence.

(8) In each of the foregoing embodiments, the traveling speed and downtime of the top board 1 are described as an example of an imaging condition. The imaging condition is not limited to them. Conducting imaging in synchronization with cardiac muscle contraction is to be described with reference to FIG. 11. As shown in FIG. 11, let a cycle of cardiac muscles be T, a number by which time division is performed on the cycle T be a gate number N, and a frame number corresponding to each cycle be F. Accordingly, imaging time (data acquisition time) is given by time per unit gate×the gate number N×the frame number F. Here, description is made to the noise equivalent count per unit area C-NEC in Embodiment 1 as one example. Where the noise equivalent count per unit area C-NEC is higher, the frame number decreases such that the total acquisition time may be reduced, or the gate number increases such that time per unit gate may be reduced. Where the noise equivalent count per unit area C-NEC is lower, the frame number increases such that the total acquisition time may extend, or the gate number decreases such that time per unit gate may extend. In this case, the data acquisition time, the gate number, or the frame number corresponds to the imaging condition in this invention.

(9) In each of the foregoing embodiments, the imaging condition setting device (the imaging condition setting section 17 in each embodiment) is provided that sets an imaging condition based on the physical quantity (the noise equivalent count C-NEC per unit area in each embodiment) for evaluating an image per size of the subject M that is calculated in the third physical quantity calculation device in this invention (the C-NEC calculation section 16d in each embodiment.) The imaging condition is automatically set. The imaging condition setting device is not necessarily provided. For instance, the physical quantity represented by the noise equivalent count C-NEC for evaluating the image may be graphically outputted and displayed on the output section represented by the monitor etc., whereby an operator manually sets the imaging condition based on the displayed physical quantity.

The invention claimed is:

1. Tomographic equipment for performing coincidence of radiation generated from a subject with radiopharmaceutical administered thereto to obtain a sectional image, comprising:
a counting device that counts radiation generated from the subject with radiopharmaceutical administered thereto;
a first physical quantity calculation device that calculates physical quantity with respect to a size of the subject;
a second physical quantity calculation device that calculates a noise equivalent count or an image noise in accordance with radiation counted by the counting device; and
a third physical quantity calculation device that calculates a noise equivalent count or an image noise per size of the subject by dividing the noise equivalent count calculated by the second physical quantity calculation device or the image noise calculated by the second physical quantity calculation device by the physical quantity calculated by the first physical quantity calculation device.

2. The tomographic equipment according to claim 1, wherein the tomographic equipment comprises an external radiation source that externally irradiates the subject with radiation of a same form as radiopharmaceutical, and the first physical quantity calculation device calculates the physical quantity with respect to a size of the subject in accordance with radiation that is applied by the external radiation source and transmitted through the subject.

3. The tomographic equipment according to claim 1, wherein the first physical quantity calculation device calculates the physical quantity with respect to the size of the subject in accordance with the form information acquired by an external equipment.

4. The tomographic equipment according to claim 3, wherein the form information is a CT image obtained with art X-ray CT equipment as the external equipment, and the first physical quantity calculation device calculates the physical quantity with respect to the size of the subject in accordance with the CT image.

5. The tomographic equipment according to claim 1, wherein the physical quantity with respect to the size of the subject calculated by the first physical quantity calculation device is a cross-sectional area of the subject.

6. The tomographic equipment according to claim 1, wherein the physical quantity with respect to the size of the subject calculated by the first physical quantity calculation device is a volume of the subject.

7. The tomographic equipment according to claim 1, wherein the tomographic equipment comprises an imaging condition setting device that sets an imaging condition in accordance with the noise equivalent count or the image noise per size of the subject calculated by the third physical quantity calculation device.

8. An imaging system with tomographic equipment that performs coincidence of radiation generated from a subject with radiopharmaceutical administered thereto to obtain a sectional image, and imaging equipment that conducts predetermined imaging to the subject for obtaining a given image, comprising:
a counting device that counts radiation generated from the subject with radiopharmaceutical administered thereto;
a first physical quantity calculation device that calculates physical quantity with respect to a size of the subject;
a second physical quantity calculation device that calculates a noise equivalent count or an image noise in accordance with radiation counted by the counting device; and
a third physical quantity calculation device that calculates a noise equivalent count or an image noise per size of the subject by dividing the noise equivalent count calculated by the second physical quantity calculation device or the image noise calculated by the second physical quantity calculation device by the physical quantity calculated by the first physical quantity calculation device.

9. The imaging system according to claim 8, wherein the tomographic equipment comprises an external radiation source that externally irradiates the subject with radiation of a same form as radiopharmaceutical, and a first physical quantity calculation device calculates the physical quantity with respect to a size of the subject in accordance with radiation that is applied by the external radiation source and transmitted through the subject.

10. The imaging system according, to claim 8, wherein the imaging equipment acquires form information on the subject, and the first physical quantity calculation device calculates the physical quantity with respect to the size of the subject in accordance with the form information.

11. The imaging system according to claim 10, wherein the imaging equipment is an X-ray CT equipment, the form information is the CT image obtained with the X-ray CT equipment, and the first physical quantity calculation device calculates the physical quantity with respect to the size of the subject in accordance with the CT image.

12. The imaging system according to claim 8, wherein the physical quantity with respect to the size of the subject calculated by the first physical quantity calculation device is a cross-sectional area of the subject.

13. The imaging system according to claim 8, wherein the physical quantity with respect to the size of the subject calculated by the first physical quantity calculation device is a volume of the subject.

14. The imaging system according to claim 8, wherein the tomographic equipment comprises an imaging condition setting device that sets an imaging condition in accordance with the noise equivalent count or the image noise per size of the subject calculated by the third physical quantity calculation device.

15. A method of acquiring imaging data by performing coincidence of radiation generated from a subject with radiopharmaceutical administered thereto, comprising:
a first physical quantity calculating step to calculate physical quantity with respect to a size of the subject with a first physical quantity calculation device,
a second physical quantity calculating step to calculate a noise equivalent count or an image noise in accordance with radiation, which is counted with a counting device that counts radiation generated from the subject with radiopharmaceutical administered thereto, with a second physical quantity calculation device, and
a third physical quantity calculating step to calculate a noise equivalent count or an image noise per size of the subject by dividing the noise equivalent count calculated by the second physical quantity calculation device or the image noise calculated by the second physical quantity calculation device by the physical quantity calculated in the first physical quantity calculating step with a third physical quantity calculation device.

16. The method of acquiring imaging data according to claim 15, comprising an imaging condition setting step to set an imaging condition in accordance with the noise equivalent count or the image noise per size of the subject calculated in the third physical quantity calculation step.

17. The method of acquiring imaging data according to claim 16, wherein imaging is conducted under the imaging condition set in the imaging condition setting step, and thereafter the first physical quantity calculation step, the second physical quantity calculation step, and the third physical quantity calculation step are repeated in accordance with the imaging data acquired in the imaging.

* * * * *